United States Patent [19]

Holtkamp, Sr.

[11] Patent Number: Plant 7,696

[45] Date of Patent: Oct. 29, 1991

[54] AFRICAN VIOLET PLANT NAMED LITTLE CHEROKEE GIRL

[76] Inventor: Reinhold Holtkamp, Sr., Blumenstrasse 28, D 4242 Rees-Haffen, Fed. Rep. of Germany

[21] Appl. No.: 565,316

[22] Filed: Aug. 10, 1990

[51] Int. Cl.[5] ..... A01H 5/00

[52] U.S. Cl. ..... Plt./69

[58] Field of Search ..... Plt./69

*Primary Examiner*—James R. Feyrer

*Attorney, Agent, or Firm*—Foley & Lardner

[57] ABSTRACT

A new and distinct cultivar of African violet named Little Cherokee Girl characterized by its mid-size growth habit (13–15 cm in diameter); pink, semi-double to double flowers; strong stems which curve toward the center to form a compact bouquet above the leaves; profuse flowering; medium green, heart shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Cherokee Girl.

The new cultivar was referred to during the breeding and selection process by the designation K 87/140 and is a product of a planned breeding program. The new cultivar was originated from a cross made by me in the controlled breeding program in Haffen, Federal Republic of Germany. The female, or seed parent was a cultivar designated K 87/3. The male, or pollen parent was a cultivar designated 43/2.

Little Cherokee Girl was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Cherokee Girl has not been observed under all possible environmental conditions. The phenotype may vary significantly with variations in environment such as temperature, light intensity and day length. The following observations, measurements and values describe the new cultivar as grown in a 5.5 cm pot in Haffen, West Germany and Nashville, Tenn. under greenhouse conditions which closely approximate those generally used in commercial practice.

The following traits have been repeatedly observed and are determined to be basic characteristics of Little Cherokee Girl, which in combination distinguish this African violet as a new and distinct cultivar:

(1) A single crown will not grow larger than 13–15 cm.

(2) Semi-double to double, pink flowers.

(3) Strong wirelike and upright flower stems curving toward the center.

(4) First flash of flowers form a tight bouquet above the leaves.

(5) Profuse flowering.

(6) Each plant carries 7–9 and more upright flower stems each of which carries 3–4 and more flowers.

(7) Long lasting, non-dropping flowers.

(8) Plant saleable 10 to 11 weeks after planting of unrooted shoot.

(9) Seed capsules push slightly through.

(10) Medium green, heart-shaped leaves are 3.5–4.0 cm in size.

(11) After maturity the flowers dry off, and remain on the peduncle without becoming infected by botrytis.

The accompanying color photographic drawing shows a typical specimen plant of the new cultivar grown in a 5.5 cm pot. The colors appearing in the photograph are as true as possible with color ilustrations of this type.

In the following description, color references are made to the Royal Horticultural Society Colour Chart (R.H.S.). except where general colors of ordinary significance are referred to. Color values were taken under natural sunlight conditions at approximately 12 a.m. in Nashville, Tenn.

Botanical Classification: *Saintpaulia ionantha,* Ramat., c.v. Little Cherokee Girl.

Parentage:

*Male parent.*—43/2.

*Female parent.*—K 87/3.

Propagation: The new cultivar holds its distinguishing characteristics through successive propagations by leaf cuttings.

Plant: From 6 cm to 8 cm tall when grown in pots, and approximately 13–15 cm in diameter when fully grown.

Leaves:

*General form.*—Heart-shaped.

*Diameter.*—35–40 mm wide and 35–40 mm long.

*Texture.*—Leatherlike.

*Aspect.*—Hairy, serrated, slightly shiny.

*Veins.*—Upperside: visible; underside: well pronounced, light green to pinkish green, shiny.

*Color (upperside).*—Yellow-Green Group 147 A.

*Color (underside).*—Greyed-Green Group 194 C with touches of Purple Group 79 A to B.

*Petiole.*—Strong, green with purplish brown touch, hairy.

Flowers:

*Buds.*—Size: 6–8 mm just before opening. Shape: Bell-shaped. Color: Pinkish Green.

*Sepals.*—Five (5). Color: Green with purplish brown touch.

*Calyx.*—Shape: Funnel-shaped. Aspect: Spear-shaped, hairy.

*Peduncle.*—Character: Strong upright, hairy. Color: Purplish brown.

Individual flowers:

*Size.*—27–32 mm.

*Shape.*—Semi-double to double.

*Color (upperside).*—Red-Purple Group 75 B to C, center 74 B. Under cooler temperatures and more intensive lighting, the pink tends to intensify.

*Color (underside).*—Purple Group 75 C to D.

*Borne.*—Each flower stem carries 3–4 and more flowers on strong, upright peduncles that are free standing above the leaves, thereby forming a compact bouquet.

*Flowering habit.*—Flowers 10–11 weeks after planting an unrooted plantlet.

Reproductive organs:

*Stamens.*—Two to four (2–4). Anthers: 2–4 composed of 4–8 anther cells, seed capsule pushes slightly through.

*Filaments.*—Yellowish green with pink on edges, 3–4 mm long.

*Styles.*—5–6 mm long, pink, base of ovary light green and hairy.

Roots: Normally developed, white when young, turning slightly brownish when older.

Disease resistance: Up to date, Little Cherokee Girl has shown very good resistance to all major violet diseases.

General observations: Little Cherokee Girl is a mid-size violet, a size between a regular violet (grown in a 10 cm pot) and a superminiature (grown in a 4 cm pot). Little Cherokee Girl is designed to be grown in a 5.5 to 6 cm pot and will not grow larger than 13–15 cm. Each of the 7–9 and more strong flower stems carries 3–4 and more pink, semi-double to double flowers. A nice bouquet of flowers free standing above the medium green, serrated, heart-shaped leaves develops approximately 10–11 weeks after planting an unrooted plantlet. The flowers have a darker center and are long-lasting and non-dropping.

I claim:

1. A new and distinct cultivar of African violet named Little Cherokee Girl, as described and illustrated, and particularly characterized by its mid-size growth habit (13–15 cm in diameter); pink, semi-double to double flowers; strong stems which curve toward the center to form a compact bouquet above the leaves; profuse flowering; medium green, heart-shaped leaves; flowering 10–11 weeks after planting of unrooted shoot, and by its long lasting and non-dropping flowers.

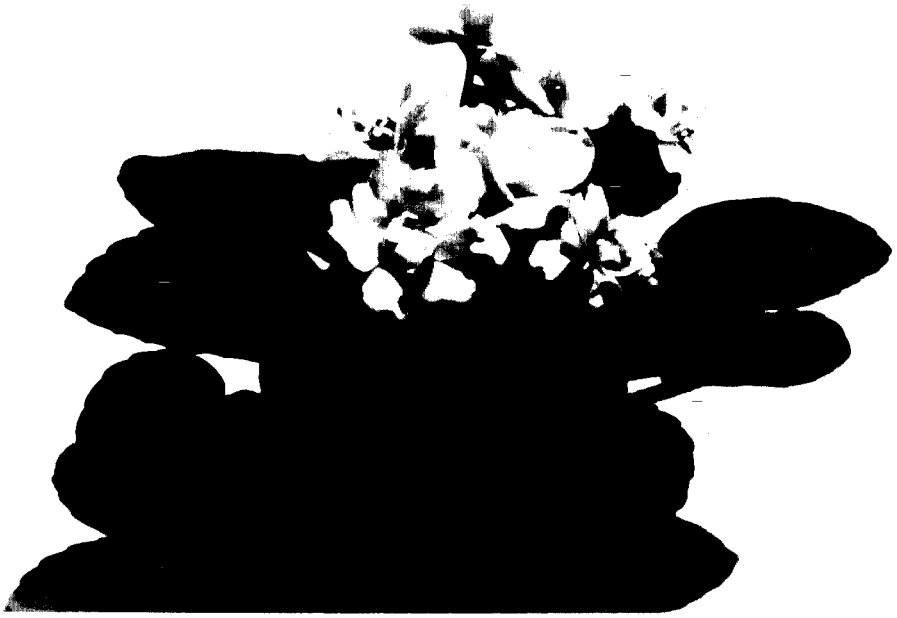

* * * * *